United States Patent
DeLeo

(10) Patent No.: US 7,285,270 B2
(45) Date of Patent: Oct. 23, 2007

(54) METHOD OF REDUCING NEUROPATHIC PAIN

(75) Inventor: Joyce A. DeLeo, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 264 days.

(21) Appl. No.: 10/521,167

(22) PCT Filed: Jul. 31, 2003

(86) PCT No.: PCT/US03/24148

§ 371 (c)(1),
(2), (4) Date: Mar. 7, 2005

(87) PCT Pub. No.: WO2004/011022

PCT Pub. Date: Feb. 5, 2004

(65) Prior Publication Data

US 2005/0158318 A1    Jul. 21, 2005

(51) Int. Cl.
*A61K 39/395* (2006.01)
(52) U.S. Cl. .................................................. 424/158.1
(58) Field of Classification Search ............... None
See application file for complete search history.

(56) References Cited

U.S. PATENT DOCUMENTS 6,312,689 B1   11/2001   LaRosa et al. ........... 424/130.1

OTHER PUBLICATIONS

Szabo I et al. Heterologous desensitization of opioid receptors by chemokines inhibits chemotaxis and enhances the perception of pain. Proc Natl Acad Sci, USA, 2002; 99(16):10276-10281.*
Flügel A et al. Neuronal MCP-1 expression in response to remote nerve injury. J. Cerebral Blood Flow Metal. 2001; 21:69-76.*
Honore P et al. Murine models of inflammatory, neuropathic and cancer pain each generates a unique set of neurochemical changes in the spinal cord and sensory neurons. Neuroscience, 2000; 98(3):585-598.*
Ogata H et al. The role of monocyte chemoattractant protein-1 (MCP-1) in the pathogenesis of collagen-induced arthritis in rats. J. Pathology, 1997; 182: 106-114.*
Winkelstein BA et al. Nerve injury proximal or distal to the DRG induces similar spinal glial activation and selective cytokine expression but differential behavioral responses to pharmacologic treatment. J. Comp. Neurol. 2001; 439:127-139.*
Abbadie et al., "Impaired neuropathic pain responses in mice lacking the chemokine receptor CCR2", Proc. Natl. Acad. Sci. USA 2003 100(13):7947-7952.

* cited by examiner

*Primary Examiner*—Elizabeth C. Kemmerer
*Assistant Examiner*—Kimberly A. Ballard
(74) *Attorney, Agent, or Firm*—Licata & TYrrell P.C.

(57) ABSTRACT

The present invention relates to methods of treating pain. Monocyte chemoattractant protein-1 (MCP-1) antibodies or binding fragments thereof are used to prevent or reduce behavioral hypersensitivity associated with pain.

1 Claim, No Drawings

METHOD OF REDUCING NEUROPATHIC PAIN

INTRODUCTION

This invention was made in the course of research sponsored by the National Institute of Drug Abuse (Grant No. DA11276). The U.S. government may have certain rights in this invention.

BACKGROUND OF THE INVENTION

Spinal neuroimmune activation and neuroinflammation following injury are associated with the development of behavioral hypersensitivity in different animal models of persistent pain states (Watkins, et al. (1995) Pain 63:289; DeLeo and Yezierski (2001) Pain 90(1-2):1-6; Winkelstein, et al. (2001) J. Comp. Neurol. 438:127-139). As such, neuroimmune activation in the central nervous system (CNS) produces glial activation and upregulation of cytokines and other regulatory proteins of the immune system (DeLeo and Yezierski (2001) supra). Spinal glial activation has been reported in rat models of neuropathy in-association with persistent behavioral hypersensitivity (Colburn, et al. (1999) Exp. Neurol. 157(2):289-304; Sweitzer, et al. (2001) J. Pharmacol. Exp. Ther. 297:1210-1217; Watkins, et al. (2001) Pain 93:201-205; Watkins, et al. (2001) Trends Neurosci. 24:450-455). Spinal cytokine (i.e., IL-1, TNF, and IL-6) mRNA and protein expression are also elevated in neuropathic injury models and exhibit a temporal relationship with behavioral hypersensitivity (DeLeo, et al. (1996) J. Interferon Cytokine Res. 16(9):695-700; Winkelstein, et al., (2001) supra; Sweitzer, et al. (2001) supra; Sweitzer, et al. (2001) Neuroscience 103:529-539). Neuroinflammation, involving the infiltration of cells into the spinal cord and DRG, occurs following nerve injury and affects behavioral hypersensitivity (Hu and McLachlan (2002) Neuroscience 112:23-28).

Emerging evidence in the literature indicates chemokines may modulate nociception (Boddeke (2001) Eur. J. Pharmacol. 429(1-3):115-119). However, while neuroinflammation implicates the upregulation of chemokines to initiate and facilitate cellular infiltration into the CNS, no study has directly investigated whether spinal chemokines are upregulated in neuropathic pain and, if so, their temporal relationship to behavioral sensitivity with this injury.

Chemokines are a subclass of cytokines involved in the activation, recruitment and infiltration of leukocytes to an injury site. They are categorized based on the presence and position of cysteine residues (Rollins (1997) Blood 90(3): 909-928; Luster (1998) N. Engl. J. Med. 338(7): 436-445). Chemokines are synthesized locally at sites of inflammation and establish concentration gradients which drive target cell migration. Chemokine receptors are expressed on neurons, astrocytes and endothelial cells (Luster (1998) N. Engl. J. Med. 338(7):436-445). Cytokines, such as IL-1 and TNF, are among the main stimuli and/or modulators for chemokine production by macrophages, dendritic cells and endothelial cells (Luster, et al. (1998) supra; Andjelkovic, et al. (1999) Glia 28:225-235; Luther and Cyster (2001) Nat. Immunol. 2:102-107). This is relevant to nerve injury-induced hypersensitivity as upregulation of these same cytokines plays a crucial role in the central neuroimmune responses of persistent pain models (Watkins, et al. (1995) supra; DeLeo and Coburn (1996) supra; DeLeo, et al. (1996) In: Low Back Pain: A Scientific and Clinical Overview, Weinstein and Gordon (eds), AAOS Publishers, Rosemont, Ill., p 163-185; Hashizume, et al. (2000) Spine 25:1206-1217; Winkelstein, et al., (2001) supra). Many chemokines, including the monocyte chemoattractant proteins (MCPS), macrophage infiltrating proteins (MIPs), and regulated upon activation, normal T-cell expressed and secreted (RANTES), have all been implicated in models of direct trauma to the CNS. Furthermore, in a peripheral experimental allergic neuritis model, mRNA expression of chemokines has been characterized using quantitative PCR methods (Fujioka, et al. (1999) J. Neurovirol. 5(1):27-31). In parallel with the documented time course of symptoms in that rat neuritis model, MCP-1, MIP-1, RANTES, and IP-10 were all increased in the cauda equina. Similarly, these same chemokines (MIP-1α, MCP-1, RANTES) were rapidly upregulated in separate central inflammatory and mechanical contusion models (Ousman and David (2001) J. Neurosci. 21(13):4649-4656; Miyasgishi, et al. (1997) J. Neuroimmunol. 77 (1):17-26; McTigue, et al. (1998) J. Neurosci. Res. 53(3):368-376). In peripheral nerve injury, MCP-1 is induced in damaged tissue (Toews, et al. (1998) J. Neurosci. Res. 53(2):260-267; Coughlan, et al. (2000) Neuroscience 97(3):591-600).

Such a chemokine response remains complicated with regards to a peripheral injury, given both its potential benefits and ill-effects. As such, a balance exists between the specific neuroprotective (beneficial) and pain-promoting (harmful) responses which result as a consequence of spinal chemokine up regulation. Spinal chemokine upregulation, specifically MCP-1, which has been demonstrated to induce monocyte/macrophage infiltration in the spinal cord (McTigue, et al. (1998) supra), can induce macrophage infiltration in a beneficial effort to promote axonal repair and healing due to the peripheral injury. This upregulation, which induces macrophage and monocyte infiltration into the spinal cord, has a beneficial effect whereby these cells promote the removal of cellular debris and facilitate axonal regeneration (Scheidt, et al. (1986) Brain Res. 379(2):380-384; Avellino, et al. (1995) Exp. Neurol. 136(2):183-198; Zeev-Brann, et al. (1998) Glia 23(3):181-190; Ma, et al. (2002) J. Neurosci. Res. 68(6):691-702). In addition, infiltrating macrophages secrete anti-inflammatory cytokines which help to reduce the overall central inflammatory response. Together, these actions of promoting axonal recovery and improved cellular survival push this "balance" to a more reparative one, which may be beneficial in achieving a state of functional survival in the CNS. In contrast, however, these same cells also contribute deleterious effects to CNS tissue influencing the balance towards a more harmful response, and can contribute to the maintenance of a pain response. Macrophages produce a host of neurotoxic mediators, including nitric oxide (Grzybicki, et al. (1998) Acta Neuropathol. (Berl). 95(1):98-103; Yamanaka, et al. (1998) Neurosci. Res. 31(4):347-350) and inflammatory cytokines, which further contribute to a deleterious cascade leading to secondary cellular damage in the spinal cord. Moreover, this same deleterious effect may contribute to the maintenance of persistent pain.

Several groups of compounds are used to relieve pain, depending on the severity and duration of the pain sensation, and on the nature of the painful stimulus. Drugs used to relieve mild, moderate or severe pain without causing unconsciousness are generally called analgesics. Mild analgesics that are termed non-narcotic agents include aspirin, acetaminophen and non-steroidal anti-inflammatory drugs. Should non-narcotic-based agents prove ineffective, narcotic/opioid analgesic agents such as morphine, codeine, meperidine, and the like are used to treat more severe acute or chronic forms of pain (Wingard, et al. (1991) Human Pharmacology: Molecular to Clinical, Mosby-Year Book, Inc., pp. 383, 391-92).

Despite the sophistication of new analgesic agents and improved understanding of the neurobiological basis of pain, current pain management treatment modalities involving narcotic, non-narcotic, and anxiolytic therapeutic agents have not been able to manage the side effect issues associated with the use of these agents. In addition, as the dizziness, drowsiness, depression, lethargy, difficulty in being mobile, weakness in the extremities, orthostatic hypotension, respiratory depression, gastrointestinal distress, and renal distress side effects of these agents occur, therapeutic regimens frequently discontinue one agent for a less successful pain control agent. Patients experiencing side effects become mal- or non-compliant in taking the prescribed pain treatment regimen to manage their particular type of pain. Finally, because of the depressive effects of these agents, healthcare personnel treat patient populations of this type more on an in-patient only setting to minimize liability issues and to monitor abuse potentials by such patients taking these particular medications.

Thus, there is a need for improved methods of treating or preventing pain.

SUMMARY OF THE INVENTION

The present invention relates to a method of preventing or treating individuals with pain. The method provides the administration of antibodies or binding fragments thereof directed to monocyte chemoattractant protein-1 (MCP-1).

These and other aspects of the present invention are set forth in more detail in the following description of the invention.

DETAILED DESCRIPTION OF THE INVENTION

The central responses specific to pain are intimately connected to the cellular responses that result from or stimulate chemokine upregulation and release. For example, chemokines induce astrocytic migration, microglial proliferation and immune cell migration, which can further exacerbate immune activation. The present invention provides a method of preventing or treating pain using antibodies to the chemokine MCP-1. The MCP-1 antibodies or binding fragments thereof of the present invention are useful to prevent and/or treat inflammatory pain or chronic pain. Inflammatory pain includes pain associated with an inflammatory process such as arthritis. Chronic pain, according to the definition proposed by the International Association for the Study of Pain, is a pain which persists beyond normal tissue healing time (suggested three months: International Association for the Study of Pain, Classification of chronic pain. Pain, 1986, Suppl. 3, S1-S226), and this implies a transition point from acute pain. Experiments, described herein, demonstrate that a MCP-1 antibody reduces behavioral sensitivity associated with pain. The spinal chemokine MCP-1 contributes to persistent behavioral sensitivity as measured by mechanical allodynia. Moreover, the temporal response of spinal chemokine mRNA expression in relation to mechanical allodynia is demonstrated.

In order to study the effects of potential agents for pain treatment, such as a MCP-1 antibody, a well established animal model of pain was used. Such animal models are routinely employed in pain research in order to both define mechanisms associated with pain in humans and to test potential treatment modalities for pain in humans. In the present invention, a mouse neuropathy model was used wherein all mice examined exhibited mechanical allodynia following L5 spinal nerve transection. A robust allodynic response was observed which was sustained over the postoperative period, for both the 0.008 (Table 1) and 0.015 (Table 2) gram von Frey filaments.

TABLE 1

| Postoperative Time (Days) | Number of Paw Withdrawals ± SEM | |
|---|---|---|
| | L5 Peripheral Spinal Nerve Transection | Sham |
| 0 | 3.52 ± 0.60 | 2.06 ± 0.19 |
| 1 | 9.96 ± 0.77 | 6.81 ± 0.86 |
| 3 | 12.54 ± 0.44 | 5.58 ± 1.17 |
| 5 | 13.15 ± 0.56 | 6.25 ± 1.23 |
| 7 | 12.54 ± 0.89 | 4.50 ± 0.78 |
| 10 | 13.17 ± 1.01 | 5.25 ± 1.60 |
| 14 | 11.33 ± 0.80 | 3.75 ± 1.93 |

TABLE 2

| Time (Days) | Number of Paw Withdrawals ± SEM | |
|---|---|---|
| | Neuropathy Model | Sham |
| 0 | 2.88 ± 0.23 | 3.06 ± 0.23 |
| 1 | 12.28 ± 0.87 | 8.00 ± 1.04 |
| 3 | 12.79 ± 0.76 | 5.92 ± 1.31 |
| 5 | 15.23 ± 0.69 | 7.88 ± 1.52 |
| 7 | 14.54 ± 0.90 | 4.75 ± 0.98 |
| 10 | 16.50 ± 0.76 | 6.00 ± 2.04 |
| 14 | 14.00 ± 0.63 | 4.75 ± 1.80 |

These responses were significantly greater (p<0.001) than those of the corresponding sham surgeries Responses were significantly elevated (p<0.034) over shams for all time points, with the exception of day 1 in the 0.008 gram testing (p=0.22).

RNAse protection assays (RPA) were performed to determine the expression of chemokines in the L5 spinal nerve transaction model. RANTES, MIP-1α/β, IP-10, and MCP-1 mRNA were constitutively expressed at low levels in normal spinal cord. Chemokines also included in the RPA analysis, not detected in this injury model, were lymphotactin/XCL1, eotaxin/CCL11, MIP-2/CXCL1, and T-Cell Activation Protein-3/CCL1. Following surgery, MIP-1α/β exhibited only slight increases compared to normal with the greatest elevation at day three. Yet, these elevations were not significant overall or at any time point following surgery (Table 3).

TABLE 3

| Time (Days) | RANTES | MIP-1β | MIP-1α | IP10 | MCP-1 |
|---|---|---|---|---|---|
| | Normal Fold Induction Over Normal | | | | |
| 1 | 1.00 ± 0.19 | 1.00 ± 0.21 | 1.00 ± 0.22 | 1.00 ± 0.24 | 1.00 ± 0.42 |
| | Neuropathy Model Fold Induction Over Normal | | | | |
| 1 | 1.38 ± 0.37 | 1.10 ± 0.27 | 1.04 ± 0.32 | 1.18 ± 0.31 | 2.43 ± 0.57 |
| 3 | 0.75 ± 0.19 | 1.28 ± 0.42 | 1.49 ± 0.60 | 1.47 ± 0.65 | 4.73 ± 0.21 |

TABLE 3-continued

| Time (Days) | RANTES | MIP-1β | MIP-1α | IP10 | MCP-1 |
|---|---|---|---|---|---|
| 7 | 2.15 ± 0.48 | 0.80 ± 0.24 | 1.31 ± 0.30 | 2.10 ± 0.52 | 4.03 ± 0.72 |
| 14 | 1.78 ± 0.35 | 1.29 ± 0.38 | 1.35 ± 0.41 | 1.31 ± 0.37 | 1.30 ± 0.43 |
| Sham Fold Induction Over Normal | | | | | |
| 1 | 1.50 ± 0.02 | 1.11 ± 0.18 | 1.16 ± 0.12 | 0.84 ± 0.04 | 1.76 ± 0.13 |
| 3 | 1.42 ± 0.55 | 0.60 ± 0.16 | 0.81 ± 0.18 | 0.72 ± 0.15 | 1.75 ± 0.79 |
| 7 | 0.95 ± 0.42 | 0.51 ± 0.55 | 0.85 ± 0.51 | 0.77 ± 0.41 | 2.49 ± 1.99 |
| 14 | 0.73 ± 0.20 | 0.78 ± 0.25 | 0.53 ± 0.22 | 0.58 ± 0.17 | 0.71 ± 0.58 |

RANTES mRNA slowly rose over normal and sham levels and was elevated more than two-fold over normal levels at days 7 and 14 for the neuropathy model. While not significant at these individual time points, the overall RANTES expression in neuropathy was significantly elevated over those levels expressed in normal spinal cord (p=0.049). However, no differences were detected between surgery and sham groups for RANTES underscoring the importance of surgical exposure. Similarly, IP-10 was elevated over normal and shams at all postoperative time points with a significant overall relationship found between the injured and sham groups (p=0.028). The peak IP-10 levels were observed on day 7, slowly rising after injury and then also exhibiting a decrease again on day 14.

The most dramatic changes in mRNA levels observed in this model were for MCP-1. Spinal MCP-1 mRNA levels in neuropathy were 2.5 times those of normal on day 1 following injury and rose to peak levels on day 3 of nearly five times those of normal. Elevated MCP-1 levels were sustained on day 7 and were nearly five times those of normal and twice those of corresponding sham levels on this day. By day 14, there was an abrupt decrease in spinal MCP-1 levels, returning to baseline. Overall, spinal MCP-1 levels following L5 spinal nerve transection were significantly greater than normal levels (p=0.004). While not significantly different from shams (p=0.18), the magnitude of these changes was robust for MCP-1, in some cases as much as 2.5 times those of sham levels. Spinal MCP-1 changes were the most immediate and the most profound of any of the chemokines probed. The results reported herein indicate a central chemokine response for a peripheral injury. Furthermore, these results indicate a role of central immune changes contributing to the mechanism of persistent pain.

RPA analysis of rat spinal cord tissue was also conducted and showed elevated MCP-1 mRNA at day 10 following surgery. Specifically, spinal MCP-1 mRNA in nerve-injured rats was 6.76±2.41 times those levels in normal, unoperated rats; which reached statistical significance (p=0.01). The relative amount of mRNA for the MCP1 receptor, CO chemokine receptor 2 (CCR2), using real time reverse transcriptase-polymerase chain reaction (RT-PCR) was also examined. Levels of CCR2 in rats with nerve transection were markedly elevated over sham and normal levels. CCR2 mRNA levels increased over normal levels as early as 4 hours following injury, reaching a peak sixfold increase at day 4. Similar results have been found in mice lacking CCR2 (Abbadle, et al. (2003) *Proc. Natl. Acad. Sci. USA* 100:7947-52). Further, the development of mechanical allodynia was totally abrogated in these CCR2-deficient mice. Sham levels at all time points of the studies conducted herein were not different from normal, yet injury produced significantly greater levels than observed for shams (p<0.006) at all time points following 4 hours. Allodynia patterns similar to those for the mice were observed for all rats receiving either sham or injury.

To examine the role of MCP-1 in modulating behavioral sensitivity in a rat neuropathy model, recombinant MCP-1 and a neutralizing antibody to MCP-1 were used to enhance and neutralize MCP-1, respectively. Intrathecal administration of the MCP-1 neutralizing antibody produced a dose-dependent attenuation of mechanical allodynia following nerve injury in tests using 2 gram (Table 4) and 12 (Table 5) gram von Frey filaments.

TABLE 4

| | Number of Paw Withdrawals ± SEM | | |
|---|---|---|---|
| Time (Days) | Vehicle-HBSS | Anti-MCP-1 20 μg | Anti-MCP-1 4 μg |
| 0 | 0.63 ± 0.26 | 1.00 ± 0.00 | 0.63 ± 0.18 |
| 1 | 9.13 ± 0.79 | 5.38 ± 0.65 | 11.25 ± 1.62 |
| 3 | 9.13 ± 1.53 | 5.63 ± 0.78 | 10.50 ± 1.15 |
| 5 | 12.63 ± 0.63 | 4.00 ± 0.42 | 10.00 ± 1.34 |
| 7 | 8.50 ± 0.78 | 3.50 ± 0.46 | 13.50 ± 1.31 |
| 10 | 9.88 ± 0.93 | 2.88 ± 0.64 | 10.75 ± 1.85 |

TABLE 5

| | Number of Paw Withdrawals ± SEM | | |
|---|---|---|---|
| Time (Days) | Vehicle-HBSS | Anti-MCP-1 20 μg | Anti-MCP-1 4 μg |
| 0 | 1.38 ± 0.38 | 1.13 ± 0.23 | 0.88 ± 0.30 |
| 1 | 10.13 ± 0.74 | 6.38 ± 0.71 | 13.38 ± 1.46 |
| 3 | 9.50 ± 1.81 | 5.00 ± 0.42 | 13.50 ± 1.27 |
| 5 | 12.63 ± 1.24 | 5.88 ± 0.48 | 13.00 ± 2.00 |
| 7 | 10.88 ± 1.25 | 4.25 ± 0.75 | 15.75 ± 1.37 |
| 10 | 11.25 ± 0.65 | 3.75 ± 0.53 | 13.38 ± 1.78 |

The low dose of 4 μg of anti-MCP-1 did not significantly alter behavioral hypersensitivity as compared to Hanks Balanced Salt Solution (HBSS) vehicle administration. However, at the higher dose of 20 μg of the MCP-1 neutralizing antibody, mechanical allodynia was significantly (p<0.001) decreased for 12 gram von Frey stimulation. A similar response was observed for 2 gram stimulation (p<0.001). These decreases were significant at days 7 (p=0.003, 2 gm; p=0.002, 12 gm) and 10 (p=0.002, 2 gm; p<0.001, 12 gm), despite terminating administration of the neutralizing antibody on day 5. Spinal MCP-1 protein levels were elevated over normal for all groups nerve-injured rats (Table 6). Moreover, no side effects were observed when anti-MCP-1 antibody was administered at either dose.

TABLE 6

| Condition | Fold-Increase |
| --- | --- |
| Normal | 1.0 ± 0.2 |
| Neuropathy - 4 µg antibody | 5.16 ± 0.72 |
| Neuropathy - 20 µg antibody | 4.60 ± 0.86 |
| Neuropathy - HBSS | 5.02 ± 0.02 |

Data shown as a ratio with normal values ± S. E. M.
Antibody - neutralizing antibody to MCP-1.

At the 50 ng dose, no changes in mechanical allodynia were observed compared to administration of the heat-inactivated recombinant MCP-1 (rMCP-1) vehicle. Overall, there was no significant difference in allodynia between the vehicle and rMCP-1 at this dose for 12 gram testing. Moreover, mechanical allodynia was not induced in the animals receiving rMCP-1 injections in the absence of neuropathy injury.

Accordingly, in a preferred embodiment MCP-1 antibodies or binding fragments thereof are used to prevent and/or treat pain. Pain is comprised of neurological pain such as neuropathies, polyneuropathies (e.g., diabetes, headache, and trauma), neuralgias (e.g., post-zosterian neuralgia, postherpetic neuralgia, trigeminal neuralgia, algodystrophy, and HIV-related pain); musculo-skeletal pain such as osteo-traumatic pain, arthritis, osteoarthritis, spondylarthritis as well as phantom limb pain, back pain, vertebral pain, chipped disc surgery failure, post-surgery pain; cancer-related pain; vascular pain such as pain resulting from Raynaud's syndrome, Horton's disease, arteritis, and varicose ulcers; as well as pain associated with multiple sclerosis, Crohn's Disease, and endometriosis.

The anti-MCP-1 antibody or binding fragment thereof of the present invention is preferably a MCP-1 neutralizing antibody or antibody fragment. By neutralization is intended the reduction in, or inhibition of a biological activity of MCP-1 as measured by an in vitro or in vivo test. For example, the induction of monocyte/macrophage infiltration in the spinal cord (McTigue, et al. (1998) *J. Neurosci. Res.* 53(3): 368-376) may be determined.

The anti-MCP-1 antibody or binding fragment thereof of the present invention may in general belong to any immunoglobulin class. Thus, for example the anti-MCP-1 antibody may be an immunoglobulin G or immunoglobulin M antibody.

The anti-MCP-1 antibody may be of animal, for example mammalian origin, and may be for example of murine, rat or human origin. The antibody may be a whole immunoglobulin, or a fragment thereof, for example a fragment derived by proteolytic cleavage of a whole antibody, such as F(ab')$_2$, Fab' or Fab fragments, or fragments obtained by recombinant DNA techniques, for example Fv fragments (as described in WO 89/02465). The antibody fragment may optionally be a single-chain antibody fragment. Alternatively, the fragment may comprise multiple chains which are linked together, for instance, by disulfide linkages. The fragment may also optionally be a multi-molecular complex. A functional antibody fragment will typically comprise at least about 50 amino acids and more typically will comprise at least about 200 amino acids. As used herein, an antibody also includes bispecific and chimeric antibodies.

The anti-MCP-1 antibody may be polyclonal or monoclonal antibodies. Antibodies particularly useful to practice the method of the invention include recombinant anti-MCP-1 antibodies and fragments thereof, i.e. anti-MCP-1 antibodies or fragments which have been produced using recombinant DNA techniques.

Especially useful recombinant antibodies include those having an antigen binding site at least part of which is derived from a different antibody, for example those in which hypervariable or complementarity determining regions of one antibody have been grafted into variable framework regions of a second, different, and preferably human, antibody (as described in EP-A-239400); recombinant antibodies or fragments wherein non-Fv sequences have been substituted by non-Fv sequences from other, different antibodies (as described in EP-A-171496, EP-A-173494 and EP-A-194276); or recombinant antibodies or fragments possessing substantially the structure of a natural immunoglobulin but wherein the hinge region has a different number of cysteine residues from that found in the natural immunoglobulin, or wherein one or more cysteine residues in a surface pocket of the recombinant antibody of fragment is in the place of another amino acid residue present in the natural immunoglobulin (as described in WO89/01974 and WO89/01782, respectively).

An effective amount of MCP-1 antibody or binding fragment thereof is defined as an amount which prevents or reduces behavioral hypersensitivity of inflammatory pain or chronic pain. Behavioral hypersensitivity of pain may include sensations that are sharp, aching, throbbing, gnawing, deep, squeezing, or colicky in nature and may be measured by, for example, exposure to thermal hyperalgesia or mechanical hyperalgesia.

As provided herein, both MCP-1 and its receptor CCR2 have elevated mRNA levels following neuropathy indicating a role in persistent pain. Therefore, as will be appreciated after reading this disclosure, one may alternatively block the receptor of MCP-1, i.e, CCR2, to prevent or treat pain. Examples of agents and antibodies specific for CCR2 which may block or inhibit the interaction between CCR2 and MCP-1 include, but are not limited to those provided by U.S. Pat. No. 6,288,103 and U.S. Pat. No. 6,458,353, respectively.

The invention is described in greater detail by the following non-limiting examples.

EXAMPLE 1

General Methods

Two sets of experiments were performed. Temporal spinal chemokine and chemokine receptor (CCR) expression in neuropathic pain was characterized and the role of spinal MCP-1 in a rodent model of persistent neuropathy was assessed. The chemokine and CCR characterization study used male C57BL/6J mice (Jackson Labs, Bar Harbor, Me.), each weighing 28-30 grams at the time of surgery and male Holtzman and Sprague-Dawley rats (Harlan, Indianapolis, Ind.), each weighing 200-250 gram at the time of surgery. For the MCP-1 study, male Holtzman rats (Harlan, Indianapolis, Ind.) were used, each weighing 200-250 gram at the time of surgery. Animals were housed individually with a 12:12 hour light:dark cycle and free access to food and water. Care was taken to minimize animal discomfort and to limit the number of animals used.

All surgical, procedures were performed under inhalation anesthesia: 3% halothane for induction and 1.5% halothane for maintenance for mice surgeries, and 4% and 2% halothane, respectively, for rat surgeries. Animals were divided into two, surgical groups: a neuropathy group having an L5 peripheral spinal nerve transection on the left side (Colburn, et al. (1997) *J. Neuroimmunol.* 79(2): 163-175) and a sham group in which the L5 nerve was exposed only. Briefly, an incision was made and muscle tissue retracted to expose the left transverse process which was then partially removed. The L5 spinal nerve was then separated from the L4 nerve and transected, removing a portion of the nerve tissue to ensure complete transection. Surgical procedures for the sham group involved the exposure of the L5 spinal nerve, without any manipulation or transection. Following surgery, wounds were irrigated with saline and the fascia and skin were closed. For mice surgeries, the fascia was closed using 7-0 silk suture and 6-0 silk suture was used for closing the skin. Similarly, in rat surgeries, 3-0 polyester suture was used to close the fascia and surgical staples were used for closing the skin. All animals were recovered in room air.

Animals were tested for mechanical allodynia with von Frey filaments (Stoelting, Wood Dale, Ill.) on the ipsilateral hind paw. Mechanical allodynia was measured as the number of hind paw withdrawals elicited by a defined non-noxious mechanical stimulus (Colburn, et al. (1997) *J. supra*). Animals were previously acclimated to the testing environment and the tester and baseline measurements were determined prior to surgery. In each testing session, animals were subjected to three rounds of ten tactile stimulations with at least ten minutes between each stimulation. Mice were tested using 0.008 and 0.015 gram von Frey filaments and rats were tested using two and 12 gram filaments. All quantification of mechanical allodynia was performed by a tester blinded to the injury type and treatment.

Data were analyzed for significance with a one-way ANOVA and post hoc Bonferroni analysis (STATA 5.0, Stata Corporation, College Station, Tex.). Significance was defined at a p value<0.05.

EXAMPLE 2

Chemokines and CCR2 in Neuropathic Pain

Following surgery, mice (n=28 neuropathy; n=12 sham) were tested for mechanical allodynia. Mechanical allodynia was measured on days 1, 3, 5, 7, 10 and 14, using the 0.008 and 0.015 gram von Frey filaments as described in Example 1.

Assessment of the temporal chemokine mRNA expression in the mouse spinal cord was performed using an RNAse Protection assay (RPA) technique. Lumbar spinal cord tissue was harvested on days 1, 3, 7, and 14. Tissue from both the neuropathy (n=7 each time point) and sham (n=3 each time point) groups were analyzed using RPA. Tissue from normal animals (n=6) was included in the RPA analysis for comparison. Isolation of mRNA and RPA were performed according to the manufacturer's directions (Pharmingen, San Diego, Calif.). The mCK-5 template set which detects Ltn, RANTES, Eotaxin, MIP-1α/β, MIP-2, IP-10, MCP-1, TCA-3, L32, and GAPDH was used for this analysis. The template set was synthesized into a $^{32}$P-labeled antisense RNA probe set, hybridized overnight with spinal RNA samples, digested with RNAse, purified, resolved on a denatured polyacrylamide gel and quantified by autoradiography. Two housekeeping genes (L32, GAPDH) were included with each sample to ensure comparative analysis of mRNA. Image analysis was employed to compare mRNA levels based on band intensities for each chemokine and injury group. The intensity of each band was measured using the public domain NIH Image software program (U.S. National Institutes of Health) and assigned an arbitrary unit based on the measured intensity levels. Image intensity for the housekeeping genes and background levels were used to normalize chemokine measurements and compare the relative levels of mRNA across groups. A time course of relative mean levels of chemokine mRNA was determined for neuropathy and the corresponding shams. Chemokine levels were normalized by the values for normal animals and reported as ratios to (fold-increases over) normal levels.

A customized RPA chemokine probe set (Pharmingen, San Diego, Calif.) for rats was utilized in a group of Holtzman rats to confirm mRNA changes in this species. Lumbar spinal cord tissue from L5 nerve-transected rats (n=5) was harvested on day 10 following injury and spinal mRNA levels were analyzed using RPA as disclosed herein. Tissue from normal animals (n=2) was also included in the RPA analysis for comparison and normalization. Isolation of mRNA and RPA were performed according to the manufacturer's directions (Pharmingen, San Diego, Calif.). A customized template set was used to probe for the following cheinokines and cytokines: MCP-1, IL-1ra, caspase-1, IL-18, MIP-2, IL-10, TNF-α, L32, and GAPDH (Pharmingen, San Diego, Calif.). Image analysis was performed using the IMAGEQUANT® software, version 5.2 (MOLECULAR DYNAMICS™, Sunnyvale, Calif.) and relative levels were compared between groups and reported as a (fold-increase over) ratio to normal levels.

EXAMPLE 3

Real Time Reverse Transcriptase Transcription-Polymerase Chain Reaction

Assessment of the temporal spinal cord CCR2 mRNA expression was performed using a Real Time Reverse Transcriptase-Polymerase Chain Reaction (RT-PCR) technique. Lumbar spinal cord tissue was harvested from Sprague-Dawley rats following L5 spinal nerve transection at four hours, 1, 4, and 7 days, respectively. Tissue from both neuropathy (n=3 each time point) and sham (n=2 each time point) groups were analyzed using RT-PCR. Tissue from normal animals (n=2) was also included for comparison. The Taqman probes/primers for CCR2 and GAPDH were designed based on Accession Nos.:NM_021866 and NM_017008 sequences, respectively, using PRIMER EXPRESS™ (APPLIED BIOSYSTEMS®, Foster City, Calif.). The forward primer for CCR2 was 5'-GAGTAACTGTGTGGT-TGACATGCA-3' (SEQ ID NO:1) while the reverse primer was 5'-GCAGCAGTGTGTCATTCCAAGA-3' (SEQ ID NO:2). The probe for CCR2 was 5'-TTAGACCAGGCCAT-GCAGGTGACAGAG-3' (SEQ ID NO:3). The forward primer for GAPDH was 5'-CCCCCAATGTATCCGT-TGTG-3' (SEQ ID NO:4) while the reverse primer was 5'-TAGCCCAGGATGCCCTTTAGT-3' (SEQ ID NO:5). The probe for GAPDH was 5'-TGCCGCCTGGAGAAAC-CTGCC-3' (SEQ ID NO:6). Probes were dually labeled with a reporter fluorescent dye, FAM (6-carboxyfluorescein), at the 5' end and a fluorescence dye quencher, TAMRA (6-carboxytetramethyl-rhodamine), at the 3' end. The specificity of the PCR primers was tested under conventional PCR conditions in a MASTERCYCLER® Gradient EPPENDORF thermocycler (Brinkmann Instrument Inc., Westbury, N.Y.). A single band with expected molecular size was observed for both CCR2 and GAPDH analyzed using 1% agarose gel electrophoresis followed by ethidium bromide staining. Prior to the reverse transcription reaction, contaminating residual genomic DNA was eliminated by DNAseI treatment of the total RNA, using DNA-FREE™ Kit (AMBION®, Austin, Tex.). RT and real time PCR reactions were carried out using the High Capacity cDNA Archive Kit (APPLIED BIOSYSTEMS®, Foster City, Calif.) and the PLATINUM® Quantitative PCR Supermix-UDG Kit (INVITROGEN™, Carlsbad, Calif.). The RT reaction was carried out in a 100 μL total reaction volume containing: 10 μL 10×RT buffer, 4 μL 25×dNTPs, 5 μL MULTISCRIBE™ reverse transcriptase (50 U/μL; APPLIED BIOSYSTEMS®, Foster City, Calif.), 21 μL RNAse-free water and 10 μg total RNA in 50 μL. The reaction was performed at 25° C. for 10 minutes, 37° C. for 120 minutes and 95° C. for 5 minutes in the MASTERCYCLER®. Real time PCR was carried out on the ICYCLER IQ™ Multicolor Real Time PCR detection system (BIO-RAD®, Hercules, Calif.), in a total reaction volume of 25 μL containing the final concentration of 1.5 U of PLATINUM® Taq DNA polymerase, 20 mM Tris-HCl (pH 8.4), 50 mM KCl, 3 mM $MgCl_2$, 200 μM dGTP, dCTP and DATP, 400 μM of dUTP and 1 U Uracyl DNA glycosylase (UDG), 200 nM of forward and reverse primers, 200 nM of Taqman probe, and 5 μL of a 10-fold dilution of cDNA from the RT step. Relative CCR2 levels were determined based on values of each sample normalized to the GAPDH housekeeping gene. The relative expression of the CCR2 mRNA was expressed as a fold-increase compared to normal values and these ratios were compared between nerve-injured and sham-operated rats.

EXAMPLE 4

Spinal MCP-1 in Neuropathic Pain

To assess the role of spinal MCP-1 in neuropathic pain, an MCP-1 neutralizing antibody and recombinant MCP-1 (rMCP-1) were each administered in separate neuropathy groups of L5 spinal nerve-injured rats. An L5 spinal nerve transection was performed for all rats. For both agents, treatment was initiated 1 hour prior to surgery and was administered postoperatively on days 1, 3, and 5 via lumbar puncture under brief inhalation anesthesia. In one subgroup of animals, the MCP-1 neutralizing antibody (Pharmingen, San Diego, Calif.) was administered at either one of two doses: a low dose of 4 μg (n=8) or a high dose of 20 μg (n=8). Also, a matched group of rats (n=8) received a 20 μl injection of Hanks Balanced Salt Solution (Gibco, Grand Island, N.Y.) as a vehicle control. In the second group of animals, either 50 ng of recombinant MCP-1 (Pharmingen, San Diego, Calif.) in 20 μL of sterile phosphate buffered saline (PBS)/1% BSA (n=8) or a heat inactivated rMCP-1 vehicle (n=8) was administered. Lastly, in a separate group of rats (n=8), 50 ng of rMCP-1 was administered in the absence of any surgery to assess the effects of spinal MCP-1 alone on mechanical allodynia. Mechanical allodynia was measured on days 1, 3, 5, 7 and 10 postoperatively for all treatment groups.

EXAMPLE 5

Enyzme-Linked Immunosorbent Assay

Quantitative determination of MCP-1 protein was performed using enzyme-linked immunosorbent assay (ELISA) for a subset of the treated rats: injured (n=4 each treatment group) and normal naïve (n=2) animals. Lumbar spinal cord was harvested on day 10. All spinal cord tissue used was flash frozen and stored at −70° C. A 0.5 cm portion of the L4-L5 region was removed from the spinal cord and homogenized in 0.20 mL of ice-cold phosphate-buffered saline (pH 7.5) containing a protease inhibitor tablet (Boehringer Mannheim, Indianapolis, Ind.). Samples were centrifuged at 12,000 rpm for 30 minutes at 4° C., aliquoted and stored at −70° C. Total protein concentration was determined using the BCA assay (Pierce, Rockland, Ill.) in accordance with the manufacturer's instructions. The MCP-1 ELISA was performed using monoclonal mouse anti-rat McP-1 and biotinylated mouse anti-rat McP-1 as capture and detection antibodies, respectively (Pharmingen, San Diego, Calif.). Recombinant rat MCP-1 (Pharmingen, San Diego, Calif.) was used to generate a standard curve ranging from 1280 to 5 pg/mL. For each tissue sample, the amount of MCP-1 protein per microgram of total protein assayed was determined. For comparison between groups, the picograms of MCP-1 per microgram of total protein were normalized by the corresponding values of tissue from normal animals. This normalized ratio indicates the fold-increase of MCP-1 following L5 spinal nerve transection over normal.

What is claimed is:

1. A method of reducing neuropathic pain characterized by an increase in monocyte chemoattractant protein-1 (MCP-1) levels in a patient in need thereof comprising administering to the patient an effective amount of antibody MCP-1 antibody or binding fragment thereof thereby reducing neuropathic pain characterized by an increase in MCP-1 levels.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
gagtaactgt gtggttgaca tgca                                          24

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
```

-continued

```
gcagcagtgt gtcattccaa ga                                              22

<210> SEQ ID NO 3
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 3
ttagaccagg ccatgcaggt gacagag                                         27

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
cccccaatgt atccgttgtg                                                 20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
tagcccagga tgccctttag t                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
tgccgcctgg agaaacctgc c                                               21
```